(12) United States Patent
Wirtz et al.

(10) Patent No.: US 8,628,525 B2
(45) Date of Patent: Jan. 14, 2014

(54) WIRELESS INTERVENTIONAL DEVICE AND A SYSTEM FOR WIRELESS ENERGY TRANSMISSION

(75) Inventors: Daniel Wirtz, Hamburg (DE); Oliver Lips, Hamburg (DE); Sascha Krueger, Hamburg (DE); Bernd David, Huettblek (DE); Steffen Weiss, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 508 days.

(21) Appl. No.: 12/519,785

(22) PCT Filed: Dec. 17, 2007

(86) PCT No.: PCT/IB2007/055143
§ 371 (c)(1),
(2), (4) Date: Jun. 18, 2009

(87) PCT Pub. No.: WO2008/078251
PCT Pub. Date: Jul. 3, 2008

(65) Prior Publication Data
US 2010/0037902 A1    Feb. 18, 2010

(30) Foreign Application Priority Data

Dec. 21, 2006  (EP) .................................. 06126778

(51) Int. Cl.
*A61B 18/18*  (2006.01)
*A61B 19/00*  (2006.01)
*A61B 5/05*  (2006.01)
*A61B 5/00*  (2006.01)

(52) U.S. Cl.
USPC ............... 606/39; 607/96; 607/101; 600/471; 600/411; 600/508; 600/13; 600/345; 600/300; 204/298.34; 324/200; 324/71.2; 324/76.11; 601/3; 128/899

(58) Field of Classification Search
USPC ........... 600/13, 411; 129/899; 601/3; 607/96, 607/471
See application file for complete search history.

(56) References Cited

U.S. PATENT DOCUMENTS

| 4,187,854 A | | 2/1980 | Hepp et al. |
| 5,245,288 A | | 9/1993 | Leussler |
| 5,437,277 A | * | 8/1995 | Dumoulin et al. ............ 600/424 |
| 5,833,603 A | | 11/1998 | Kovacs et al. |

(Continued)

FOREIGN PATENT DOCUMENTS

| WO | WO0016686 | 3/2000 |
| WO | WO03032002 | 4/2003 |
| WO | WO2005120336 | 12/2005 |

OTHER PUBLICATIONS

J.F.L. Goose et al., "Silicon Sensors for Use in Catheters", 1st Annual international IEEE-EMBS Special Topic Conference on Micro Technologies in Medicine and Microbiology, Oct. 12-14, Lyon, France, 2000.

*Primary Examiner* — Christine Matthews
*Assistant Examiner* — Sunita Reddy

(57) ABSTRACT

An interventional device (12) is configured to be positioned in a body and includes an electrically operable unit (E1, E2) configured to carry out an interaction with the body upon a receipt of electric power. The device further includes a sensor (2) configured for wirelessly receiving electromagnetic energy from a remote source. The sensor is configured as a resonant circuit (2a, 2b) which converts the received electromagnetic energy into the electric power. The electrically operable device may include a diagnostic and/or therapeutic module.

20 Claims, 3 Drawing Sheets

(56) References Cited

U.S. PATENT DOCUMENTS

| | | | |
|---|---|---|---|
| 5,876,338 A * | 3/1999 | Gilderdale et al. | 600/411 |
| 6,015,387 A | 1/2000 | Schwartz et al. | |
| 6,236,205 B1 | 5/2001 | Ludeke et al. | |
| 6,246,896 B1 * | 6/2001 | Dumoulin et al. | 600/411 |
| 6,393,314 B1 * | 5/2002 | Watkins et al. | 600/411 |
| 6,464,687 B1 | 10/2002 | Ishikawa et al. | |
| 6,474,341 B1 | 11/2002 | Hunter et al. | |
| 6,496,714 B1 * | 12/2002 | Weiss et al. | 600/423 |
| 6,605,085 B1 * | 8/2003 | Edwards | 606/41 |
| 2002/0138009 A1 * | 9/2002 | Brockway et al. | 600/485 |
| 2005/0099290 A1 * | 5/2005 | Govari | 340/539.13 |
| 2005/0115542 A1 | 6/2005 | Hochstrasser et al. | |
| 2005/0159789 A1 * | 7/2005 | Brockway et al. | 607/32 |
| 2006/0079793 A1 * | 4/2006 | Mann et al. | 600/486 |
| 2006/0206170 A1 | 9/2006 | Denker et al. | |
| 2008/0097227 A1 * | 4/2008 | Zdeblick et al. | 600/486 |
| 2008/0136416 A1 * | 6/2008 | Goetz et al. | 324/322 |

\* cited by examiner

WIRELESS INTERVENTIONAL DEVICE AND A SYSTEM FOR WIRELESS ENERGY TRANSMISSION

BACKGROUND

The invention relates to an interventional device conceived to be positioned in a body and comprising an electrically operable unit conceived to carry out an interaction with the body upon a receipt of electric power.

The invention still further relates to a system for wireless energy transmission.

An embodiment of the interventional device is known per se and comprises an interventional catheter provided, for example, with a set of coils arranged to produce a local field distortion for purposes of catheter tracking in the body under magnetic resonance imaging. The coils are electrically fed by means of dedicated wiring running along the catheter. The known interventional device is widely applicable for a wide range of applications, including cardiac interventions.

It is a disadvantage of the known interventional device that health hazards may occur for the patient in case the intervention is carried out under supervision of magnetic resonance imaging due to application of MR imaging pulses and resulting undesirable interaction between the electromagnetic RF pulses and wiring feeding the electrodes.

SUMMARY

It is an object of the invention to provide an interventional device wherein safety aspects pertaining to the operation of the electrically operable unit are improved.

To this end the interventional device according to the invention further comprises a sensor arranged for wirelessly receiving electromagnetic energy from a remote source, the said sensor being arranged as a resonant circuit and being conceived to convert the received electromagnetic energy into the said electric power.

The technical measure of the invention is based on the insight that by means of arranging at least the sensor of the device as a resonant circuit and by supplying the energy received by the sensor wirelessly, the safety aspects with regard to possible health hazards are improved. The energy received by the sensor is made available to the electrically operable unit incorporated in the interventional device. In particular, safety aspects of use of the interventional device during interventions under inspection by means of magnetic resonance imaging are improved. Since there are no wires attached for powering the sensors, there will be no heating, notably at the distal end and at the tip of the catheter containing the electrically operable unit which might otherwise be severe and dangerous to patients.

For efficient energy reception the resonant frequency of the sensor is tuned to the frequency of a suitable transmitter. Preferably, the transmitter is arranged as a resonant circuit as well. By arranging the interventional device with the electrically operable unit for interacting with the body as being powered wirelessly, a well controlled and safe system for interventional patient interaction is produced due to absence of powered wiring inside the patient. In the interventional wireless device according to the invention all interactions with the patient's body are performed on demand by energizing the electrically operable unit so that no unnecessary hazard to the patient's health occurs.

An embodiment of a wireless interventional device is known from U.S. Pat. No. 6,474, 341 B1. The known device comprises an interventional catheter arranged with a sensor for receipt of electromagnetic energy from a remotely arranged source. The known catheter is arranged with the sensor for enabling position tracking of the catheter. For this purpose magnetic fields are projected into an anatomical body to induce voltage signals in a sensing coil of the catheter that are sufficient to describe its position. The voltage signals are wirelessly retransmitted by the sensor as positional signals indicative of a current location of the sensor in the anatomical body. For this purpose the known catheter comprises a transmission and processing unit. The transmission and processing unit may be energized by the powering signals received by the sensor, which are supplied to the transmitter in a suitable way.

Although the document U.S. Pat. No. 6,474,341 B1 discloses an operational mode of the interventional device when the sensor is designed as a resonant circuit, the document U.S. Pat. No. 6,474,341 B1 only teaches power supply in order to enable continuous emission of the position signals. The present invention, however, concerns providing pulses of energy to perform some interaction with the body. In this respect, the circuit receiving electromagnetic energy that in turn powers the electrically operable unit interacting with the body needs to satisfy different specifications. For example, in case when the electrically operable unit is used for purposes of cardiac pacing, the current feeding the pacer, ranges approximately from 0.1 to 10 mA. Together with a typical impedance (several 100 Ohms+some ten pF capacitance at 64 MHz) of healthy human tissue this yields the voltages necessary. The duration of a single pulse is preferably selected between 0.1 and 10 ms, with 2 ms being a typical value. Most commercial stimulators provide a delay time of 10-1000 ms between pulses and various possibilities of defining trains of pulses combined in one cycle, and all of that for several channels. For providing the currents mentioned above an arrangement using a diode in conjunction with a capacitor is suitable. Repetitions and delays would be steered by switching power transmission on and off Power electronics and amps fast enough for this are available, for example the electronics and amplifiers used for transmitting the RF for MR-imaging. For other embodiments of the electrically operable unit, the necessary current feeding it is approximately within the same range of 0.1 to 10 mA.

In an embodiment of the device according to the invention the device comprises an interventional catheter and the electrically operable unit comprises a therapeutic module.

Preferably, the therapeutic module comprises a cardiac pacing or ablation device. Using Magnetic Resonance (MR) as an imaging modality for catheter interventions brings about strong restrictions for the equipment used, since highly conducting structures inside of an MR-machine are hazardous because of RF-heating. Thus standard catheters used for X-Ray fluoroscopy are not safely usable for MR since conducting wires are employed for signal transmission. Especially during cardiac interventions a catheter has to provide three basic functionalities: mapping of ECG-signals, transmitting pacing signals as well as RF-power for ablation. While ECG-mapping can be made RF-safe using highly resistive wires, providing secure power transmission is more difficult. The proposed way of transmitting power to the tip electrode of an RF-safe catheter (e.g. for cardiac pacing) is based upon RF-transmission using a dedicated sensor arranged as a resonant circuit. RF-safety for power transmission can be provided by completely avoiding hazardous wires. Power transmission to the catheter is done employing one or more transmit-antennas outside the body whose signal is picked up by a resonant circuit at the catheter tip. By doing so all basic signal transmission functionalities of an EP catheter can be made RF-safe and hereby opening this imaging modality for this application. Moreover the realization of the pickup-circuitry at the catheter tip is cost-effective and easy to realize making the proposed invention especially suitable for disposable devices like EP-catheters. The setup may preferably include two resonant circuits, one on the transmitter side and one on the sensor side. One or more antenna(s) are located outside the body and are used for RF power transmission while the sensor is located at the tip of the catheter used for pacing. It includes a resonant circuit tuned to the same frequency as the transmitter so that it can pick up incident RF-power without any substantial power loss. This RF-power, once stored in the resonator is then for example, rectified using a diode and a low-pass filter is used to extract a DC-pulse. The latter is passed on to a pair of electrodes that deliver the energy to the patient tissue.

In a further embodiment of the device according to the invention the device comprises an interventional catheter and the electrically operable unit comprises a diagnostic module.

Suitable examples for diagnostic modules that might be operated at the tip of a catheter and that would need an external power supply may comprise the following:

a sensor for determining the blood pressure and/or partial pressure of e.g. O2.
  related to the pressure sensor is the measurement of blood flow which would be useful for judging the degree of a stenosis.
  a sensor for determining the temperature. This might be especially useful when combining the pacing concept with ablation. Then it is of great interest to have reliable temperature information in order to be able to estimate the degree of damage done to the tissue. While the output-signal could be transmitted in several ways (wireless, using highly resistive wires, by optical methods, etc.) providing a DC power supply can be done using a rectified RF-power signal. It is also noted that the interventional device according to the invention may comprise a plurality of diagnostic modules. Suitable examples of a plurality of diagnostic modules arranged within an interventional catheter is known from J. F. L. Goose et al "Silicon Sensors for use in Catheters", 1st Annual International IEEE-EMBS Special Topic Conference on Micro technologies in Medicine and Microbiology, October 12-14, Lyon, 2000, France In a further embodiment of the interventional device according to the invention the resonant circuit is arranged to operate at Larmor frequency.

Operating at the Larmor frequency is advantageous, as the receive circuit can absorb energy delivered e.g. by the quadrature body coil (QBC) or any other transmit coil at MR frequency. The duration of RF-transmission then defines the length of the pacing pulse. In this scenario pacing would have to be interleaved with imaging. During the imaging phases the resonant circuit would have to be detuned using e.g. a varactor diode. In order to minimize the interference of the RF for pacing with the spin system, preferably, a RF pacing frequency is used that is at the very edge of the resonance of the loaded QBC, but far off the water resonance in case no gradients are present.

It is noted that for MR applications, when transmitting power at Larmor-frequency, a detuning of the pickup-circuit comparable to that used in surface coils should be performed during imaging. The resonance frequency of the receiver has to be shifted several MHz away from the Larmor-frequency during imaging. The exact number is dependent on the width of the transmission/reception curve. If the resonator is of high quality the transmission curve becomes very narrow, sufficient detuning is achieved easily by shifting this curve by a few MHz. When the quality of the receiving circuit becomes worse, for example due to resistive losses, the curve broadens and for efficient detuning the frequency shift has to be greater. The latter will be the case for the receiver on a catheter tip which will be of rather poor quality (due to its size and the close contact to tissue/body liquids). In any case, according to empirical expertise, the detuning circuit should preferably reduce the (power-) sensitivity at the operating frequency by about 30 dB.

In a still further embodiment of the interventional device according to the invention, the resonant circuit is arranged to operate at a frequency, substantially different from the Larmor-frequency.

With regards to RF-safety operating the power transmission off the Larmor-frequency is more preferable. This could be achieved by selecting an operational frequency either above or below the Larmor-frequency. To the high-frequency end the absorption of human tissue would set a natural boundary for operation since enough power has to reach the receiver. It is found that that operation up to GHz-frequencies should be possible.

On the lower end the antenna design and the physiological effectiveness of the transmitted power will probably set the limits. Thus from several 100 kHz onwards the concept should work in principal.

For avoiding interference with the imaging and safety problems, the term 'substantially different' should be understood as a frequency selection when a power pickup compared to that at Larmor-frequency is reduced by about 30 dB. Depending on the exact properties of the circuitry this determines the necessary frequency shift.

This operational mode ensures substantially no disturbance to MR imaging. Imaging and pacing can thus be performed independently. In case of cardiac pacing, for example, the pulse length can be tailored by switching the transmitter on and off. In both cases rectification and low pass filtering extracts the desired DC pulse that is the envelope of the RF-signal.

When transmitting off the MR-frequency, it is also possible to use the rectified current for visualization of an active tracking catheter. Alternative to delivering the voltage to a pair of electrodes as described above, a properly designed inductive element, for example, a coil is placed at that position. The resulting artifact in the image created by the DC-current flowing through the inductance can be used to actively track the catheter tip.

Preferably, for ensuring a substantially orientation invariant receipt of the powering signal, the sensor of the interventional device according to the invention comprises a plurality of coils being arranged in a mutually non-planar configuration.

A system for wireless transmission of electromagnetic power to an interventional device according to the invention comprises a wireless transmitter and the interventional device according to the foregoing.

These and other aspects of the invention will be described in more detail with reference to figures.

DETAILED DESCRIPTION OF EMBODIMENTS

Figure 1:
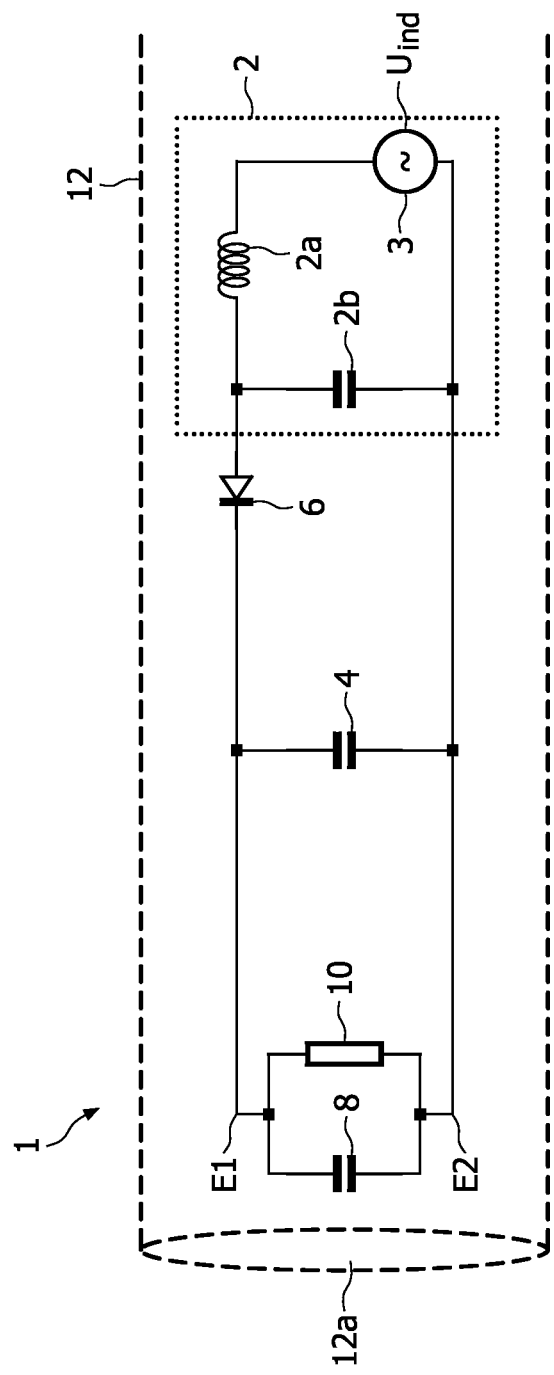
FIG. 1 presents in a schematic way an embodiment of the interventional device according to the invention, said device operating at off-Larmor frequency.

FIG. 1 presents in a schematic way an embodiment of the interventional device according to the invention, said device operating at off-Larmor frequency. The central component of the invention is the receiver circuit located at the tip 12a of the catheter 12. A schematic realization as a Spice circuit is shown in FIG. 1, which in this particular embodiment is appropriate for transmitting off the MR-frequency only. Otherwise, when operating at the Larmor frequency, the circuit gets more complex due to the need for detuning while signal transmission for imaging is on.

In accordance with FIG. 1, for pickup of the signal 3 a resonant structure 2 comprising a suitable inductor 2a and a capacitance 2b is needed. The inductance 2a is preferably dimensioned in a way that the induced voltage is in the order of 10V. This can be realized with a coil of some 10 windings on a 9F (3 mm) catheter assuming a Q-factor of the resonance circuit of 30 and an incident $B_1$-field of 1 µT at the position of the device at 1.5 T. The strength of the available $B_1$-field can be increased using several transmitters.

Care has to be taken of the following: while operating a catheter equipped with the pacing mechanism as proposed above the orientation of the inductor in the receiving circuit with regards to the external transmitter can change. This would result in a change in the induced voltage. One way of compensating for this problem is to use a number of transmit coils (not shown) located at right angles to each other or at least a non-planar configuration of the transmitter.

Additionally or alternatively, the catheter 12 could also be equipped with orthogonal saddle coils and two rectifier circuits to overcome the orientation problem. Moreover the quadrature body coil (QBC) can be used for transmission (in this case at Larmor frequency) providing a circular polarized RF-field. This would also advantageously assist in providing sufficient RF-power that the sensor can pick up.

In case of using the QBC, field strengths of around 20 µT at 1.5 T are available thus reducing the number of windings needed. Having the RF energy stored in the resonant circuit formed by the capacitance 2b and the inductance 2a it is then transferred to a pair of electrodes E1,E2. Using a diode 6 and a low-pass circuit, for example a shunt capacitance 4, the RF pulse is rectified and filtered such that the DC-waveform is extracted. In FIG. 1, capacitor 8 and resistor 10 represent typical values describing the complex impedance of the human tissue in contact with the catheter tip. The real part of the complex impedance described by resistor 10 is several 100 Ohms, while the imaginary part described by the capacitor 8 is about 15 pF for typical frequencies used for MR imaging.

Figure 2:
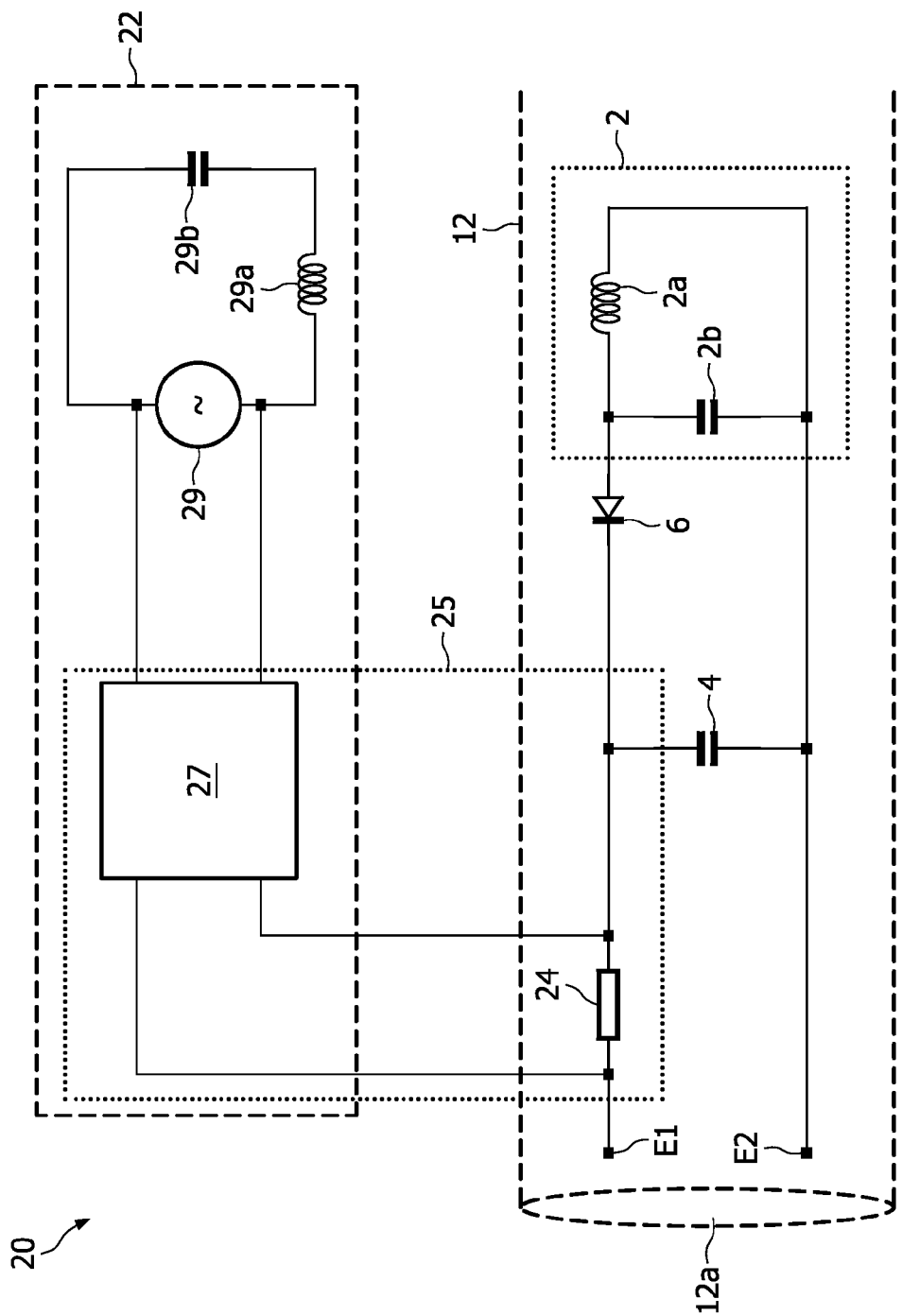
FIG. 2 presents in a schematic way an embodiment of the system according to the invention.

FIG. 2 presents in a schematic way an embodiment of the system according to the invention. The system (all of FIG. 2) comprises an interventional device, notably a catheter 12 comprising electrodes E1 and E2, other parts being the same, as discussed with reference to FIG. 1. The system 20 (see above) further comprises a wireless transmitter 22, comprising a power supply unit 29 and a transmitter arranged as a resonant circuit with an inductive element 29a and a capacitive element 29b. The system 20 (see above) further comprises a feed-back loop 25 and a control unit 27 arranged to tune the power unit 29 in accordance with the power transmitted to the electrodes E1, E2.

The voltage present at the electrode E1 is advantageously monitored by the feed-back loop 25 due to the problem of varying orientation of the receive coil with respect to the transmission field. Preferably, highly resistive wires are used for this purpose. The monitoring would allow creating a feedback loop that adjusts the transmitted power level to the actual receiver position. Moreover, for interventional applications, the tissue parameters cannot be regarded as constant with the result of changing impedance between the electrodes. The feedback is also arranged to compensate for this effect. The voltage across a resistance 24 inserted right behind electrode E1 can be measured in an MR-safe manner employing per se known highly resistive wires. The voltage measured across resistor 24 is fed to a control unit that generates a time dependent error signal comparing the input to a pre-selected voltage. The error signal is modified in an appropriate way and used to steer the power source driving the resonant transmitter circuit which in turn delivers the RF power to the receiver at the tip of the catheter.

Figure 3:
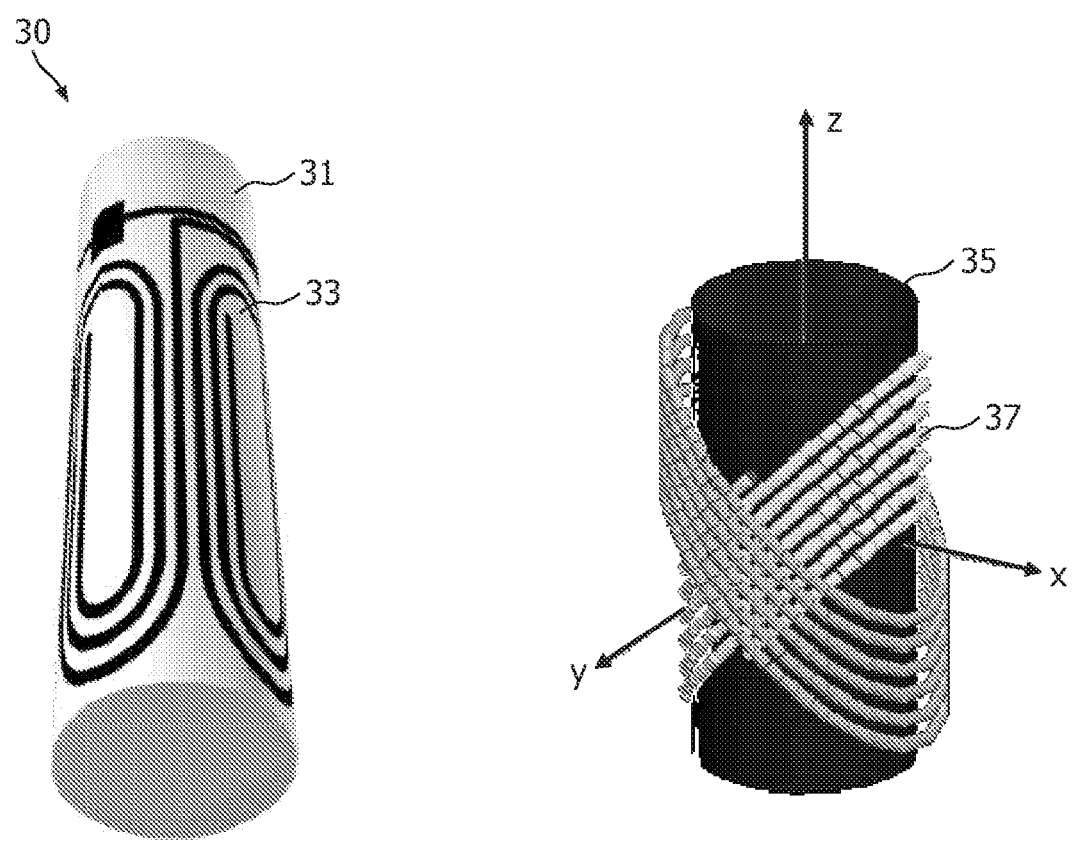
FIG. 3 presents a schematic view of the non-planar sensor configuration.

FIG. 3 presents a schematic view of the non-planar sensor configuration. It is found to be advantageous to arrange the wiring of the coil of the receiver in substantially non-planar configuration. FIG. 3 presents in a schematic view an embodiment of such suitable configuration, wherein an interventional catheter 31 is arranged with a sensor in a saddle-like configuration 33. Another suitable embodiment of a non-planar arrangement of the wiring of the sensor forming the resonant circuit is shown for a catheter 35 with a spirally arranged wiring 37. By using either spatially crossed diagonal coils 37 or the saddle coil 33, a receiver provided that is sensitive to a planar transmitter in any orientation.

While the invention has been illustrated and described in detail in the drawings and foregoing description, such illustration and description are to be considered illustrative or exemplary and not restrictive; the invention is not limited to the disclosed embodiments.

The invention claimed is:

1. An MR compatible interventional system comprising:
   an interventional catheter configured to be inserted in a human body located in a body coil of a magnetic resonance imager, the interventional catheter including:
   an electrically powered unit which carries out an interaction with an interior of the body,
   a resonant circuit which wirelessly receives RF electromagnetic energy, and converts the received RF electromagnetic energy into electric power,
   a remote unit remote from the interventional catheter and connected by only resistive wires with the interventional catheter, the resistive wires carrying feedback signals indicative of an amount of the electric power wirelessly delivered to the electrically powered unit by the resonant circuit, the remote unit including:
   an RF transmitter which generates the RF electromagnetic energy received by the resonant circuit, and
   a controller which controls the RF transmitter to control an amount of power in the generated RF electromagnetic energy in accordance with the feedback signals.

2. The MR compatible interventional system according to claim 1, wherein the resonant circuit is disposed at a tip of the interventional catheter.

3. The MR compatible interventional system according to claim 1, wherein the electrically powered unit includes at least one of a therapeutic module and a diagnostic module connected to receive the electric power from the resonant circuit.

4. The MR compatible interventional system according to claim 1, wherein the resonant circuit is tuned to a Larmor frequeney of the magnetic resonance imager in which the interventional catheter is positioned.

5. The MR compatible interventional system according claim 1, wherein the resonant circuit is tuned to a frequency, sufficiently above a Larmor frequency of the magnetic resonance imager in which the interventional catheter is positioned such that a power pick up compared to the Larmor frequency is reduced by at least 30 dB.

6. The MR compatible interventional system according to claim 5, wherein the electrically powered unit comprises;
an inductive element which produces a local magnetic field upon being energized by said electric power.

7. The MR compatible interventional system according to claim 1, wherein the resonant circuit comprises:
a plurality of coils being arranged in a mutually non-planar configuration; and
wherein the RF transmitter includes a transmit coil arranged in a non-planar configuration.

8. The MR compatible interventional system according to claim 1, wherein the resonant circuit is disposed at a tip of the interventional catheter such that the electric power is supplied via the received RF electromagnetic energy without wires running along the catheter to supply the electric power.

9. An interventional system comprising:
an interventional catheter including;
a receive coil disposed at a tip of the interventional catheter and tuned to a preselected frequency such that the receive coil receives RF signals and converts the received RF signals to electric power without wires running along the interventional catheter,
electrodes connected with the receive coil such that the electrodes receive the electric power from the receive coil,
a measuring unit which measures level of the electric power at the electrodes;
a remote unit remote from the interventional catheter, the remote unit including:
a transmitter which transmits the RF Signals at the preselected frequency with an adjustable level of power,
a controller which compares the measured level of the electric power supplied to the electrodes with a preselected level of the electric power and adjusts a delivered level of RF transmit power with which the transmitter transmits the RF signals in accordance with an error between the measured level of power and the preselected level of power.

10. The interventional system according to claim 9, further including:
resistance wires connected to the measuring unit and the controller, the resistance wires feeding back the measured level of power to the controller.

11. The interventional system according to claim 10, wherein the interventional catheter is configured to be disposed in a magnetic resonance imaging system and wherein the wires are highly resistive.

12. The interventional system according to claim 9, wherein the interventional system further includes:
a rectifier and filter connected between the receive coil and the electrodes such that DC power is delivered to the electrodes.

13. The interventional system according to claim 12, further including:
a therapeutic or diagnostic module connected with the electrodes such that the module receives the preselected level of the electric power.

14. The interventional system according to claim 13, wherein the interventional catheter is configured to be inserted into a human body and wherein the therapeutic or diagnostic module is disposed adjacent the tip of the catheter to interact with the human body into which the catheter is inserted.

15. The interventional system according to claim 9, wherein the receive coil includes:
one of spatially crossed coils or saddle coils in a non-planar configuration.

16. The interventional system according to claim 9, wherein the interventional catheter receives the electrical power from the remote unit only via the RF signals transmitted from the transmitter without electrical power carring wires running a length of the catheter.

17. The interventional system according to claim 16, wherein the transmitter includes a planar transmit coil, and the receive coil includes non-planar coil elements shaped to be sensitive to the RF signals transmitted from the transmitter when the coil elements are in any orientation.

18. The interventional system according to claim 17, wherein the planar transmit coil and the receive coil are tuned to a frequency of at least a GHz.

19. An interventional system comprising:
an interventional catheter including:
a receive coil tuned to a preselected frequency with a capacitor connected with the receive coil such that the receive coil receives RF signals and converts the received RF signals to electric power,
first and second electrodes connected with the receive coil by a first line connected with a first of the first and second electrodes and with a second line connected to a second of the first and second electrodes such that the first and second electrodes receive the electric power from the receive coil;
a diode and a shunt capacitor connected with the first and second lines to rectify the electric power to a DC wave form;
a measuring unit which measures a level of the electric power at the electrodes, the measuring unit being connected between the shunt capacitor and the diode and at least one of the electrodes.

20. The interventional system according to claim 19, further including:
a remote unit remote from the interventional catheter, the remote unit including:
a transmitter which transmits an RF signal at the preselected frequency with an adjustable level of power,
a controller which compares the measured level of the electric power supplied to the electrodes with a preselected level of the electric power and adjusts a delivered level of RF transmit power with which the transmitter transmits the RF signal in accordance with an error between the measured level of power and the preselected level of power.

* * * * *